US00PP26959P2

(12) United States Plant Patent
Jacobs

(10) Patent No.: US PP26,959 P2
(45) Date of Patent: Jul. 19, 2016

(54) *ALSTROEMERIA* PLANT NAMED 'ZALSACHARM'

(50) Latin Name: *Alstroemeria hybrida*
Varietal Denomination: Zalsacharm

(71) Applicant: Henricus Cornelius Maria Jacobs, Bleiswijk (NL)

(72) Inventor: Henricus Cornelius Maria Jacobs, Bleiswijk (NL)

(73) Assignee: Van Zanten Plants B.V., Rijsenhout (NL)

( * ) Notice: Subject to any disclaimer, the term of this patent is extended or adjusted under 35 U.S.C. 154(b) by 26 days.

(21) Appl. No.: 14/121,890

(22) Filed: Oct. 31, 2014

(51) Int. Cl.
*A01H 5/02* (2006.01)

(52) U.S. Cl.
USPC ..... Plt./309

(58) Field of Classification Search
USPC ..... Plt./309
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Alstroemeria* plant named 'Zalsacharm', characterized by its erect and strong flowering stems; moderately vigorous growth habit; large white-colored flowers with green-colored venation that face mostly upright; excellent postproduction longevity; and relative tolerance to high temperatures.

2 Drawing Sheets

Botanical designation: *Alstroemeria hybrida.*
Cultivar denomination: 'ZALSACHARM'.

BACKGROUND OF THE INVENTION

The present invention relates to a new and distinct cultivar of *Alstroemeria* plant, botanically known as *Alstroemeria hybrida*, commercially used as a cut flower *Alstroemeria*, and hereinafter referred to by the name 'Zalsacharm'.

The new *Alstroemeria* plant is a product of a planned breeding program conducted by the Inventor in Rijsenhout, The Netherlands. The objective of the breeding program is to create new cut flower *Alstroemeria* plants with desirable flower and plant qualities, attractive and unique flower coloration and excellent postproduction longevity.

The new *Alstroemeria* plant originated from a cross-pollination made by the Inventor in Rijsenhout, The Netherlands in June, 2009 of a proprietary *Alstroemeria hybrida* selection identified as code number 52969-1, not patented, as the female, or seed, parent with a proprietary *Alstroemeria hybrida* selection identified as code number 72343-1, not patented, as the male, or pollen, parent. The new *Alstroemeria* plant was discovered and selected by the Inventor as a single flowering plant from within the progeny of the stated cross-pollination in a controlled greenhouse environment in Rijsenhout, The Netherlands in June, 2010.

Asexual reproduction of the new *Alstroemeria* plant by rhizome divisions in a controlled greenhouse environment in Rijsenhout, The Netherlands since September, 2010 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'Zalsacharm'. These characteristics in combination distinguish 'Zalsacharm' as a new and distinct *Alstroemeria* plant:

1. Erect and strong flowering stems.
2. Moderately vigorous growth habit.
3. Large white-colored flowers with green-colored venation that face mostly upright.
4. Excellent postproduction longevity.
5. Relatively tolerant to high temperatures.

Plants of the new *Alstroemeria* can be compared to plants of the female parent selection. Plants of the new *Alstroemeria* differ from plants of the female parent selection primarily in flower reproductive structures as plants of the female parent selection have fully formed reproductive structures whereas plants of the new *Alstroemeria* either do not form reproductive structures or form rudimentary reproductive structures.

Plants of the new *Alstroemeria* can be compared to plants of the male parent selection. Plants of the new *Alstroemeria* differ from plants of the male parent selection primarily in flower reproductive structures as plants of the male parent selection have fully formed reproductive structures whereas plants of the new *Alstroemeria* either do not form reproductive structures or form rudimentary reproductive structures. In addition, plants of the new *Alstroemeria* differ from plants of the male parent selection in flower color as plants of the male parent selection have yellow-colored flowers.

Plants of the new *Alstroemeria* can be compared to plants of *Alstroemeria hybrida* 'Zalsabri', disclosed in U.S. Plant Pat. No. 25,213. In side-by-side comparisons conducted in Rijsenhout, The Netherlands, plants of the new *Alstroemeria* differed primarily from plants of 'Zalsabri' in the following characteristics:

1. Plants of the new *Alstroemeria* were shorter than plants of 'Zalsabri'.

2. Plants of the new *Alstroemeria* were not as vigorous as plants of 'Zalsabri'.
3. Plants of the new *Alstroemeria* had narrower leaves than plants of 'Zalsabri'.
4. Plants of the new *Alstroemeria* had larger flowers than plants of 'Zalsabri'.
5. Flowers of plants of the new *Alstroemeria* and 'Zalsabri' differed in flower color as plants of 'Zalsabri' had pink-colored flowers.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet comprises a close-up view of a typical flowering stem of 'Zalsacharm'.

The photograph on the second sheet is a close-up view of typical flowers of 'Zalsacharm'.

DETAILED BOTANICAL DESCRIPTION

The aforementioned photographs and following observations and measurements describe plants of the new *Alstroemeria* grown during the late summer in ground beds in a glass-covered greenhouse in Rijsenhout, The Netherlands. During the production of the plants, day temperatures ranged from 15° C. to 25° C., night temperatures ranged from 10° C. to 15° C., soil temperatures averaged 14° C. and light levels averaged 5,000 lux. Plants were six months old when the photographs and description were taken. In the following description, color references are made to The Royal Horticultural Society Colour Chart, 2007 Edition, except where general terms of ordinary dictionary significance are used.

Botanical classification: *Alstroemeria hybrida* 'Zalsacharm'.

Parentage:

*Female, or seed, parent*.—Proprietary *Alstroemeria hybrida* selection identified as code number 52969-1, not patented.

*Male, or pollen, parent*.—Proprietary *Alstroemeria hybrida* selection identified as code number 72343-1, not patented.

Propagation:

*Type*.—In vitro rhizogenesis.

*Time to produce a rooted young plant, summer*.—About 40 days at temperatures of 16° C. to 25° C.

*Time to produce a rooted young plant, winter*.—About 60 days at temperatures of 16° C. to 20° C.

*Root description*.—Fibrous, fleshy, thick; color, close to 155D.

*Rooting habit*.—Freely branching; medium density.

*Rhizomes*.—Shape: Elongate; rounded. Length: About 10 cm to 30 cm. Diameter: About 3 mm to 10 mm. Texture: Smooth. Color: Close to 155D.

Plant description:

*Plant and growth habit*.—Upright; freely branching, bushy appearance; moderately vigorous growth habit; rapid growth rate.

*Plant height*.—About 120 cm to 125 cm.

*Plant diameter* (*spread*).—About 20 cm.

Flowering stem description:

*Aspect*.—Erect.

*Length*.—About 105 cm to 110 cm.

*Diameter*.—About 7 mm to 10 mm.

*Internode length*.—About 0.5 cm to 8 cm.

*Strength*.—Strong.

*Texture*.—Smooth, glabrous.

*Color*.—Close to 146B.

Leaf description:

*Appearance*.—Leaves asymmetrical, simple; sessile.

*Length*.—About 13.3 cm to 16.8 cm.

*Width*.—About 3 cm to 4 cm.

*Shape*.—Lanceolate.

*Apex*.—Acute.

*Base*.—Cuneate.

*Margin*.—Entire; slightly undulate.

*Texture, upper and lower surfaces*.—Smooth, glabrous.

*Venation pattern*.—Parallel.

*Color*.—Developing and fully developed leaves, upper surface: Close to N137B; venation, close to 144C. Developing and fully developed leaves, lower surface: Close to N137D; venation, close to 144B.

Flower description:

*Flower type and habit*.—Single cup-shaped flowers arranged in compound umbels; flowers face mostly upright to outwardly; perianth segments separate; freely flowering habit, about 36 to 56 flower buds and open flowers developing per flowering stem.

*Natural flowering season*.—Flowering continuous during the spring in The Netherlands; plants begin flowering about 80 to 90 days after planting.

*Fragrance*.—None detected.

*Flower longevity*.—About four weeks on the plant and about 25 to 28 days as a cut flower; flowers not persistent.

*Flower buds* (*showing color*).—Length: About 4.5 cm. Diameter: About 2.3 cm. Shape: Roughly ovoid. Color: Close to 144A.

*Umbel height*.—About 24 cm to 29 cm.

*Umbel diameter*.—About 15 cm to 18 cm.

*Flower diameter*.—About 5.8 cm.

*Flower depth*.—About 4.5 cm.

*Perianth*.—Arrangement: Six arranged in two whorls, each whorl with two lateral and one median segments. Inner perianth, lateral segments: Length: About 3.1 cm to 4.2 cm. Width: About 1.2 cm to 2.1 cm. Shape: Oblanceolate. Apex: Wishbone-shaped. Base: Cuneate. Margin: Entire. Texture, upper and lower surfaces: Smooth, glabrous. Color, when opening and fully opened, upper surface: Close to NN155D; center, close to 3D; towards the apex, close to 63B; occasional stripes, close to 187B. Color, when opening and fully opened, lower surface: Close to NN155D; towards the apex and venation, close to 143B. Inner perianth, median segment: Length: About 3 cm to 4.4 cm. Width: About 1.2 cm to 2.4 cm. Shape: Oblanceolate. Apex: Wishbone-shaped. Base: Cuneate. Margin: Entire. Texture, upper and lower surfaces: Smooth, glabrous. Color, when opening and fully opened, upper surface: Close to NN155D; towards the apex, close to 63B. Color, when opening and fully opened, lower surface: Close to NN155D; towards the apex and venation, close to 143B. Outer perianth, lateral segments: Length: About 4 cm to 5.4 cm. Width: About 3.1 cm to 4 cm. Shape: Obovate. Apex: Embedded point. Base: Cuneate. Margin: Entire. Texture, upper and lower surfaces: Smooth, glabrous.

Color, when opening and fully opened, upper surface: Close to NN155D; towards the apex, close to 63B. Color, when opening and fully opened, lower surface: Close to NN155D; towards the apex, close to 143A; venation, close to 143B. Outer perianth, median segment: Length: About 4.4 cm to 5.1 cm. Width: About 3.1 cm to 4 cm. Shape: Obovate. Apex: Embedded point. Base: Cuneate. Margin: Entire. Texture, upper and lower surfaces: Smooth, glabrous. Color, when opening and fully opened, upper surface: Close to NN155D; towards the apex, close to 63B. Color, when opening and fully opened, lower surface: Close to NN155D; towards the apex, close to 143A; venation, close to 143B.

*Pedicels*.—Length: About 2.1 cm to 6.5 cm. Diameter: About 3 mm to 4 mm. Strength: Strong. Angle: About 10° to 15° from vertical. Texture: Smooth, glabrous. Color, upper and lower surfaces: Close to 146B.

*Reproductive structures*.—Stamens: Typically not formed or inconspicuous rudimentary structures. Pistils: Typically not formed or inconspicuous rudimentary structures. Seeds and fruits: Seed and fruit development has not been observed on plants of the new *Alstroemeria*.

Disease & pest resistance: Plants of the new *Alstroemeria* have not been observed to be resistant to pathogens and pests common to *Alstroemeria* plants.

Temperature tolerance: Plants of the new *Alstroemeria* have been observed to tolerate temperatures from about −5° C. to about 40° C.

It is claimed:

1. A new and distinct *Alstroemeria* plant named 'Zalsacharm' as illustrated and described.

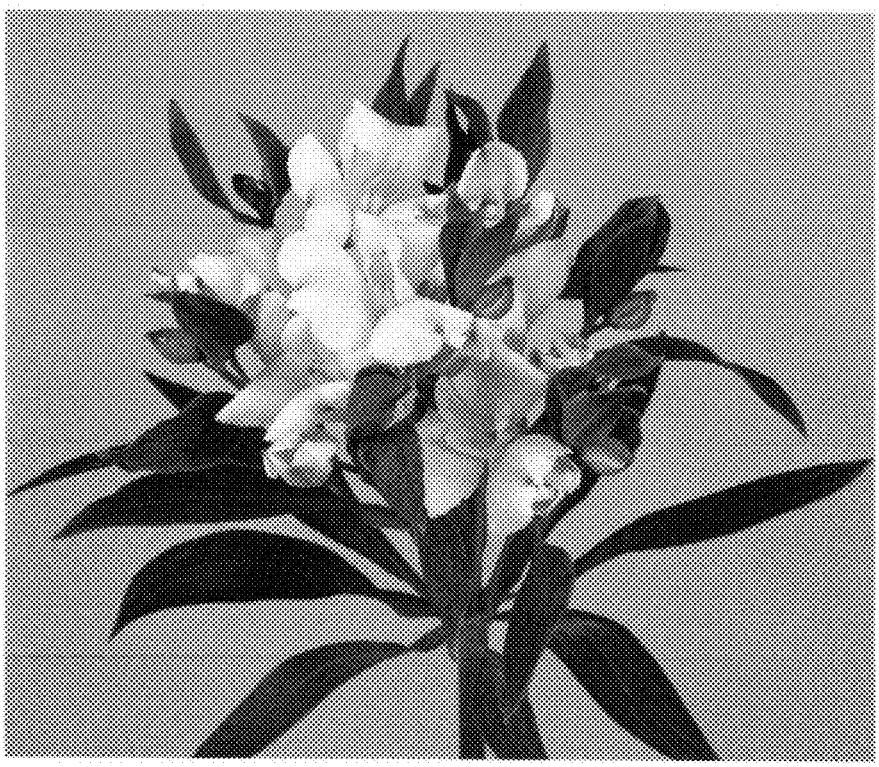

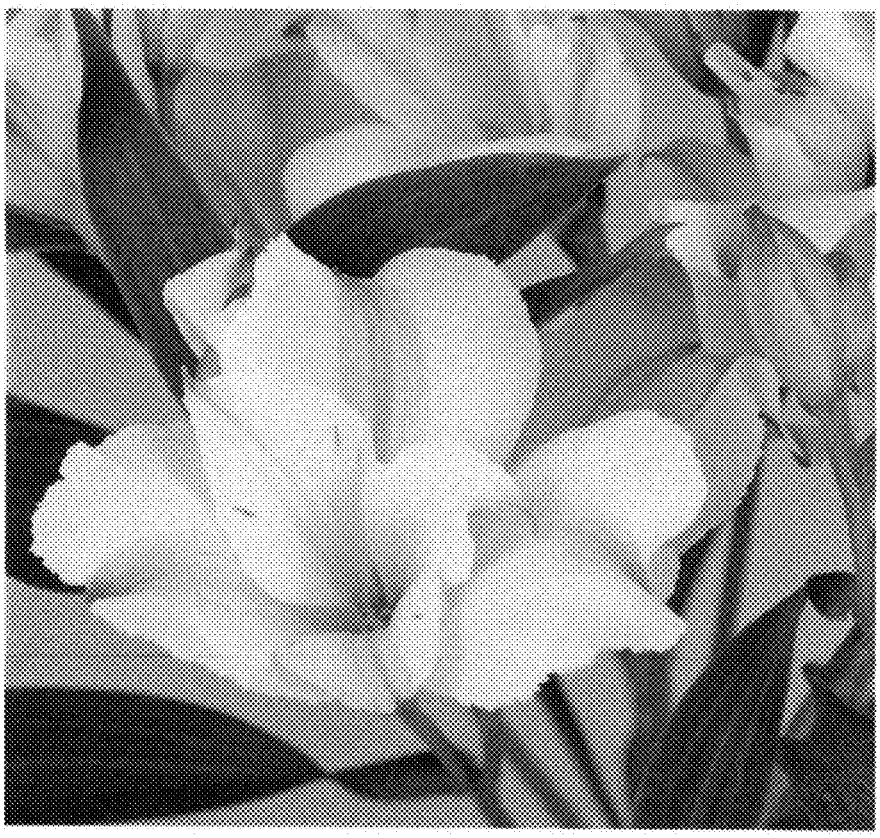

* * * * *